United States Patent
Hoda et al.

(10) Patent No.: US 9,618,480 B2
(45) Date of Patent: Apr. 11, 2017

(54) METHOD AND APPARATUS FOR INSPECTING WELD QUALITY

(71) Applicant: Hitachi, Ltd, Tokyo (JP)

(72) Inventors: Isao Hoda, Novi, MI (US); Hua Zeng, Novi, MI (US); Masayoshi Takahashi, Yokohama (JP); Hiroki Funato, Chigasaki (JP)

(73) Assignee: Hitachi, Ltd., Tokyo (JP)

( * ) Notice: Subject to any disclaimer, the term of this patent is extended or adjusted under 35 U.S.C. 154(b) by 29 days.

(21) Appl. No.: 14/847,751

(22) Filed: Sep. 8, 2015

(65) Prior Publication Data

US 2017/0067854 A1   Mar. 9, 2017

(51) Int. Cl.
| | |
|---|---|
| *G01N 27/82* | (2006.01) |
| *G01N 27/83* | (2006.01) |
| *B23K 31/12* | (2006.01) |
| *G01N 27/90* | (2006.01) |
| *G01N 27/72* | (2006.01) |
| *G01R 33/12* | (2006.01) |

(52) U.S. Cl.
CPC ............ *G01N 27/82* (2013.01); *B23K 31/125* (2013.01); *G01N 27/72* (2013.01); *G01N 27/9046* (2013.01); *G01R 33/12* (2013.01)

(58) Field of Classification Search
CPC ..... G01N 27/9046; G01N 27/72; G01R 33/12
USPC .................................................. 324/238, 240
See application file for complete search history.

(56) References Cited

U.S. PATENT DOCUMENTS

| | | | | |
|---|---|---|---|---|
| 4,414,508 | A * | 11/1983 | Davis ................ | G01N 27/9046 324/219 |
| 6,952,095 | B1 * | 10/2005 | Goldfine ................. | G01B 7/24 324/202 |
| 7,230,421 | B2 * | 6/2007 | Goldfine ................. | G01B 7/24 324/240 |

FOREIGN PATENT DOCUMENTS

JP        5261763 B2    8/2013

* cited by examiner

*Primary Examiner* — Reena Aurora
(74) *Attorney, Agent, or Firm* — Mattingly & Malur, PC

(57) ABSTRACT

An apparatus and method for inspecting the quality of a weld under test in a structure having a plurality of spaced apart welds. Two probes are placed on opposite sides of the structure so that a current path is formed through the weld under test. The probes are energized with alternating current at a known frequency. The magnetic flux generated from the current flow through the probes and at least one of the spaced apart welds is then measured and subsequently compared with magnetic flux data previously determined and representing weld quality.

14 Claims, 2 Drawing Sheets

METHOD AND APPARATUS FOR INSPECTING WELD QUALITY

BACKGROUND OF THE INVENTION

I. Field of the Invention

The present invention relates to an apparatus and method for inspecting the quality of a weld.

II. Description of Related Art

There are many different industries, such as the automotive industry, in which two components are secured together by spaced apart welds in order to form a structure. In the automotive industry, many of the car panels are welded together in this fashion.

As long as the welds provide for good electrical contact between the two components in the structure, electromagnetic noise is dissipated and presents little problem. However, when one or more of the welds become corroded or otherwise defective so that the weld presents a point of high resistance, rather than low resistance, electrical noise may be propagated by the panels. Such electrical noise can cause interference with the infotainment systems of the vehicle, as well as other undesirable results. Consequently, it has become important to inspect the qualities of the welds in a structure to determine if any of the welds exhibit poor contact caused by rust or otherwise.

Previously, there has been no simple way to measure the contact impedance of the individual welds in a structure having a plurality of spaced apart welds. As such, it has been difficult, if not impossible, to identify and correct faulty welds in the structure.

SUMMARY OF THE PRESENT INVENTION

The present invention provides an apparatus for inspecting the quality of a weld in a structure having two components secured together by a plurality of spaced apart welds.

In brief, in the present invention, two probes are placed on opposite sides of the structure and so that the weld under test is positioned in between the two welds. Consequently, in the event that the weld exhibits low impedance, indicative that the weld is of high quality, most of the current passing from one probe to the other probe will pass directly through the weld under test.

Conversely, in the event that the weld under test has a higher impedance caused, for example, by rust, a significant portion of the current flow from one probe and to the other probe will not pass through the weld under test. Instead, this substantial portion of the current will pass along the structure and through the adjacent weld or welds and back to the other probe.

In order to detect this current flow from the probes and to the adjacent spaced apart welds, at least one, and preferably several coils are positioned around the weld under test so that the magnetic flux generated by current flow from the probes and to the adjacent spaced apart welds will pass through the coils. This, in turn, generates a voltage signal which is measurable and which varies in magnitude proportionately with the magnitude of the flux flowing through the coil.

The probes are electrically energized at a known frequency, for example between 1 hertz and 100 kilohertz. If the weld under test is of poor quality, the current flow from the weld under test to adjacent welds will also generate magnetic flux which flows through one or more of the coils.

While the alternating current is applied to the probes, the current flux through the coil or coils is then measured and subsequently compared with previously determined data indicative of the quality of the weld. This previously determined data is preferably determined empirically, although such data may alternatively be also mathematically derived.

In the event that more accurate measurements are required, a reference coil is positioned adjacent one of the probes so that flux generated by current flow through the probe will flow through the reference coil. However, the reference coil is spaced sufficiently from the structure so that any flux generated by current flow between the probe and the spaced apart welds will be negligible. This reference data may then be used to correct the data measurements made by the other coils.

BRIEF DESCRIPTION OF THE DRAWING

A better understanding of the present invention will be had upon reference to the following detailed description when read in conjunction with the accompanying drawing, wherein like reference characters refer to like parts throughout the several views, and in which.

DETAILED DESCRIPTION OF PREFERRED EMBODIMENTS OF THE PRESENT INVENTION

Figure 1:
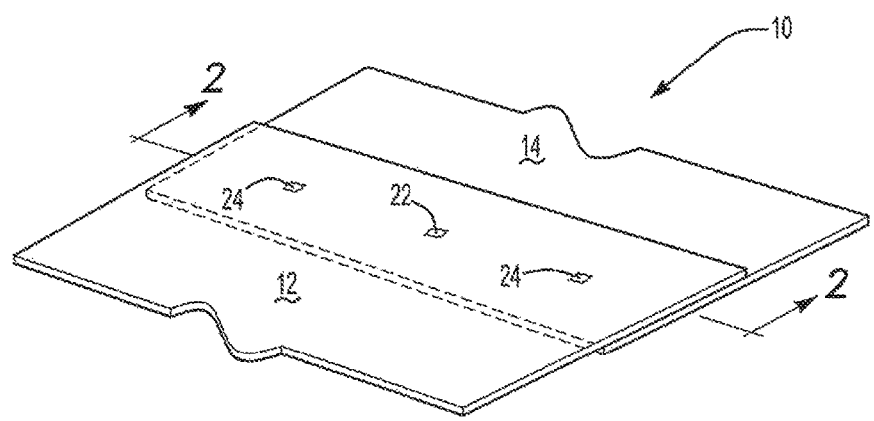
FIG. 1 is a top fragmentary diagrammatic view illustrating an exemplary structure.

With reference first to FIG. 1, a metal structure 10 is shown constructed from two metal components 12 and 14. These metal components 12 and 14 may be of any conventional type, such as two automotive body panels.

In order to secure the components 12 and 14 together, a plurality of spot welds 22 and 24 extend through both components 12 and 14 and secure them together.

Although the welds 22 and 24 are preferably spot welds, alternatively they may comprise a threaded metallic fastener, such as a bolt and nut or a rivet. Consequently, as used in this patent, the term "weld" means any metallic connector for securing two components together at spaced intervals to form a structure.

Figure 2:
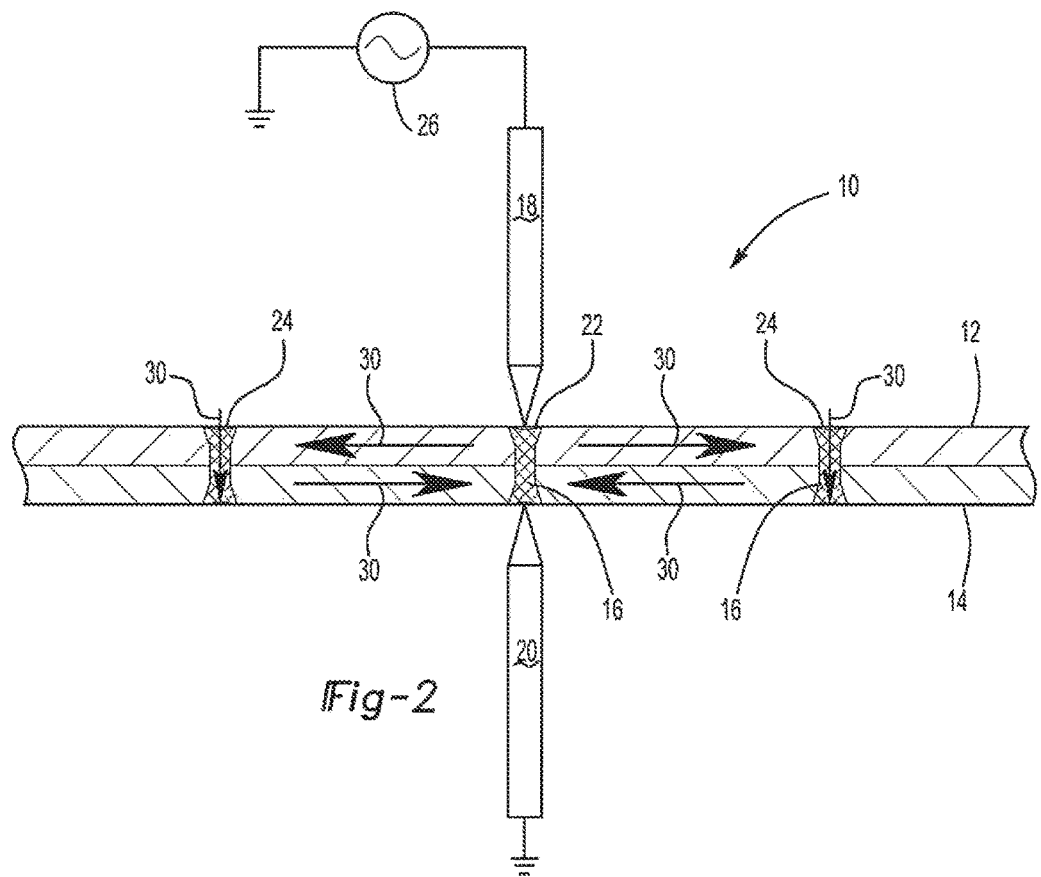
FIG. 2 is a fragmentary side view illustrating current flow through the structure as a result of an AC current generator.

With reference now particularly to FIG. 2, in order to test the quality of the welds 22, two probes 18 and 20 are positioned on opposite sides of the structure 10 and in alignment with the weld 22 under test. The other welds 24 are spaced apart from the weld under test 22.

Still referring to FIG. 2, an alternating current source 26 produces alternating current at a known frequency. This frequency may vary, e.g. from 1 hertz to 1 kilohertz, and the AC source is connected in series with the probes 18 and 20. Consequently, if the weld under test 22 is of high quality, i.e. it exhibits little impedance, substantially all of the current from the current source 26 flows through the probes 18 and 20 and the weld under test 22.

Conversely, if the weld under test 22 is of poor quality, e.g. rusty or otherwise defective, the weld under test 22 will exhibit a high impedance. Consequently, when the AC current source 26 is applied to the probes 18 and 20, a significant amount of current flows along the structure components 12 and 14 and through the spaced apart welds 24 as shown by arrows 30. Such current flow assumes, of course, that the spaced apart welds 24 are of higher quality, and thus lower impedance, than the weld under test 22. Consequently, in order to determine the quality of the weld under test 22, it is necessary only to measure the current flow along the structure 10 and through the adjacent welds 30 and then compare that current flow with empirical data representative of weld quality to determine the quality of the weld under test 22.

Figure 3:
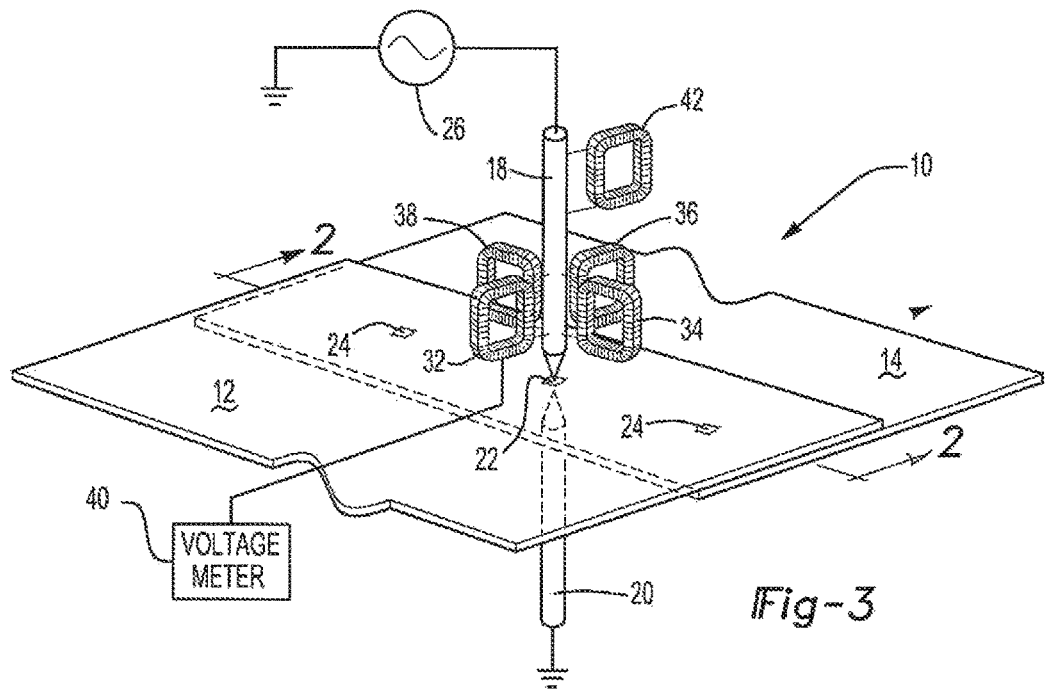
FIG. 3 is an elevational view illustrating a preferred embodiment of the present invention.

With reference now to FIG. 3, in order to measure the current flow along the structure 10 and to the spaced apart welds 24 at least one, and preferably four coils 32, 34, 36, and 38 are circumferentially spaced, preferably equally spaced, from each other around the probe 18. Furthermore, preferably at least two of the coils 34 and 38 lie in a plane that is parallel to a line drawn between the two spaced apart welds 24. These coils 32-38, furthermore, are electrically connected to a voltage meter 40.

Assuming that the weld under test 22 is of high quality, most of the current flow from the current source 26 passes directly through the weld under test 22. In this event, the only inductance measured by the voltage meter 40 will be the inductance created by the alternating current flow through the weld under test 22, the probes 18 and 20, and detected by the four coils 32-38. This voltage, furthermore, may be compared to previously determined or historical data, preferably empirically determined, to determine that the weld under test 22 is of high quality. Assuming that the coils 32-38 are substantially the same, each will generate substantially the same current.

Conversely, in the event that the weld under test 22 is of poor quality, e.g. rusted, and thus exhibits a high impedance, current flows not only through the probes 18 and 20, but also along the components 12 and 14 and through the spaced apart welds 24 as shown by arrows 30 (FIG. 2). When this occurs, the current flow from the probes 18 and 20 to the spaced apart welds 24 will also create magnetic flux that is detected by the coils 32-38. In particular, the coils 34 and 38 that lie in a plane that is perpendicular to the flux generated by the current flow between the probes 18 and 20 and the spaced apart welds 24 should generate more current than the other two coils 32 and 36. When this occurs, the voltage meter 40 will measure a higher voltage and this higher voltage is then compared to previously determined data, preferably empirically determined, to determine the quality of the weld under test 22.

If high accuracy measurements are required, a reference coil 42 may be positioned adjacent the probe 18 so that flux generated by the probe 18 when energized by alternating current will flow through the reference coil 42. However, the reference coil 42 is sufficiently spaced from the structure 10 so that magnetic flux produced by current flow between the probes 18 and 20 and the spaced apart welds 24, if present, will be minimal at the position of the reference coil 42 and thus produce a negligible voltage.

In this fashion, the output voltage produced by the reference coil 42 is only indicative of the flux produced by the current flow through the probes 18 and 20. This value may then be used to correct or adjust the voltages obtained from the coils 32-38 for an accurate reading of the magnitude of the current flow through the spaced apart welds.

Figure 4A:
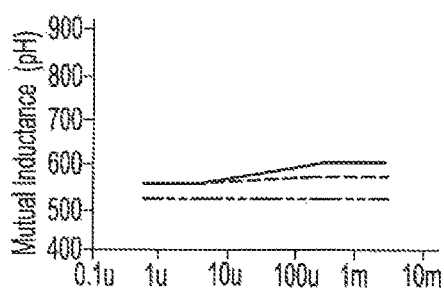
FIGS. 4A and 4B are graphs illustrating the increase in mutual inductance versus contact impedance for the weld under test.
Figure 4B:
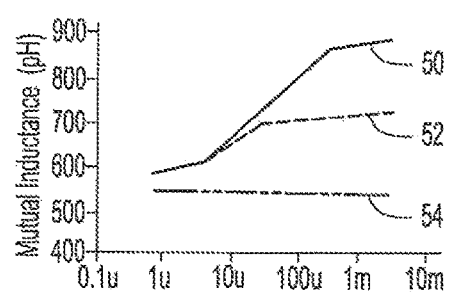

With reference now to FIGS. 4A and 4B, two graphs are shown illustrating the effect of an increase of the impedance on the mutual inductance sensed by the coils 32-38. Specifically, FIG. 4A illustrates the magnitude of the inductance sensed by the coils 32 and 36 while FIG. 4B illustrates the increase in mutual inductance sensed by the coils 34 and 38 as the contact impedance of the weld under test increases. Thus, it can be seen that the coils that lie in a plane that is perpendicular to the flux generated by current flow between the probes and the spaced apart welds exhibit higher mutual inductance as the contact impedance increases as opposed to the coils 32 and 36 which lie in the plane parallel to the magnetic flux generated by the current flow between the probe and the spaced apart welds 22.

For example, in FIG. 4B graph 50 illustrates the increase in the mutual inductance for a 1 hertz signal. Similarly, graph 52 illustrates the increase in mutual inductance at a frequency of 10 hertz for the alternating current generator 26. Graph 54 represents the mutual inductance as a function of contact impedance where the AC current generator frequency is 100 kilohertz. As can be seen, the increase in mutual inductance at high frequencies such as 100 kilohertz is negligible despite an increase in the contact impedance.

Conversely, FIG. 4A shows only a minor increase of the mutual inductance as a function of the increase in contact impedance for the coils 32 and 36. Such limited mutual inductance is expected since the magnetic flux generated by the current flow from the probes 18 and 20 and to the spaced apart welds is generally parallel to the coils 32 and 36.

From the foregoing, it can be seen that the present invention provides a simple yet effective way for determining the quality of welds in a structure having a plurality of spaced apart welds. Having described our invention, however, many modifications thereto will become apparent to those skilled in the art to which it pertains without deviation from the spirit of the invention as defined by the scope of the appended claims.

We claim:

1. A method for inspecting the quality of a weld under test in a structure having a plurality of spaced apart welds comprising the steps of:
   placing two probes on opposite sides of the structure so that a current path is formed through the weld under test,
   energizing the probes with alternating current at least one known frequency,
   measuring magnetic flux generated from current flow through said probes and at least one spaced apart weld,
   comparing said measured magnetic flux with previously determined data representing weld quality to thereby determine the weld quality of the weld under test.

2. The method as defined in claim 1 wherein said measuring step comprises the step of positioning at least one coil along the structure such that magnetic flux caused by current flow through said probes and one of said plurality of spaced apart welds passes through said coil.

3. The method as defined in claim 2 wherein said coil comprises a plurality of coils.

4. The method as defined in claim 3 wherein said coils are positioned around one of said probes and circumferentially spaced from each other.

5. The method as defined in claim 4 wherein magnetic flux generated by current flow through said probes and the weld under test passes through at least one of said coils.

6. The method as defined in claim 3 wherein at least one of said coils lies in a plane substantially parallel to a line extending between the weld under test and one of said spaced apart welds.

7. The method as defined in claim 1 and comprising the steps of:
   placing a reference coil so that magnetic flux generated by current flow through the probes passes through the reference coil but sufficiently spaced from a current path between the probes and one spaced apart weld so that flux generated by current flow between the probes and said one spaced apart weld is negligible, and measuring magnetic flux with said reference coil, comparing the measured magnetic flux through said reference coil with said previously determined data representing weld quality to thereby determine the weld quality of the weld under test.

8. The apparatus as defined in claim 1 wherein said sensor comprises a coil positioned along the structure such that magnetic flux caused by current flow through said probes and one of said plurality of spaced apart welds passes through said coil.

9. The apparatus method as defined in claim 8 wherein said coil comprises a plurality of coils.

10. The apparatus as defined in claim 9 wherein said coils are positioned around one of said probes and circumferentially spaced from each other.

11. The apparatus as defined in claim 10 wherein magnetic flux generated by current flow through said probes and the weld under test passes through at least one of said coils.

12. The apparatus as defined in claim 8 and comprising:

a reference coil positioned so that magnetic flux generated by current flow through the probes passes through the reference coil but sufficiently spaced from a current path between the probes and one spaced apart weld so that flux generated by current flow between the probes and said one spaced apart weld is negligible, and wherein the magnetic flux flowing through said reference coil is compared with said previously determined data representing weld quality to thereby determine the weld quality of the weld under test.

13. The apparatus as defined in claim 9 wherein at least one of said coils lies in a plane substantially parallel to a line extending between the weld under test and one of said spaced apart welds.

14. Apparatus for inspecting the quality of a weld under test in a structure having a plurality of spaced apart welds comprising:

two probes on opposite sides of the structure so that a current path is formed through the weld under test, an alternating power source having at least one known frequency, said power source connected to said probes, a sensor which measures magnetic flux generated from current flow through said probes and at least one spaced apart weld, wherein said measured magnetic flux is compared with previously determined data representing weld quality to thereby determine the weld quality of the weld under test.

* * * * *